United States Patent [19]

Shinohara et al.

[11] Patent Number: 4,634,790

[45] Date of Patent: Jan. 6, 1987

[54] PROCESS FOR PRODUCING α-L-ASPARTYL-L-PHENYLALANINE METHYL ESTER OR ITS HYDROHALIDE

[75] Inventors: Emiko Shinohara, Saga; Katsumi Sugiyama, Yokosuka; Masanao Ozaki, Yokohama; Keizo Matsuda, Kawasaki, all of Japan

[73] Assignee: Ajinomoto Co., Inc., Tokyo, Japan

[21] Appl. No.: 700,034

[22] Filed: Feb. 11, 1985

[30] Foreign Application Priority Data

Feb. 21, 1984 [JP] Japan ................................. 59-30987

[51] Int. Cl.[4] ....................... C07C 101/32; C07K 5/06
[52] U.S. Cl. .................................. 560/40; 260/998.21
[58] Field of Search ..................... 260/112.5 R, 998.21; 560/40

[56] References Cited

U.S. PATENT DOCUMENTS 3,962,207  6/1976  Uchiyama et al. ........... 260/112.5 R Primary Examiner—Delbert R. Phillips
Attorney, Agent, or Firm—Oblon, Fisher, Spivak, McClelland, & Maier

[57] ABSTRACT

A process for producing α-L-aspartyl-L-phenylalanine methyl ester or its hydrohalide, which comprises subjecting 3-benzyl-6-carboxymethyl-2,5-diketopiperazine to partial hydrolysis with a strong acid in a solvent mixture of methanol and water.

4 Claims, No Drawings

PROCESS FOR PRODUCING α-L-ASPARTYL-L-PHENYLALANINE METHYL ESTER OR ITS HYDROHALIDE

DETAILED DESCRIPTION OF THE INVENTION

The present invention relates to a process for producing α-L-aspartyl-L-phenylalanine methyl ester.

α-L-Aspartyl-L-phenylalanine methyl ester (hereinafter simply referred to as "α-APM") is a useful substance to which attention has been given due to its sweet taste of good quality.

As processes for advantageously synthesizing this substance, there are known, for example, a process which comprises binding an N-protected-L-aspartic anhydride to L-phenylalanine methyl ester in an organic solvent and then splitting the substituent off in a conventional manner (U.S. Pat. No. 3,786,039), a process which comprises directly binding a strong acid addition salt of L-aspartic anhydride to L-phenylalanine methyl ester (Japanese Examined Patent Publication 14217/74), a process which comprises condensing an N-protected-L-aspartic acid to L-phenylalanine methyl ester in the presence of enzyme (Japanese Examined Patent Publication 135595/80), etc.

However, α-APM is a dipeptide ester having an α-bond. For this reason, α-APM readily changes to 3-benzyl-6-carboxymethyl-2,5-diketopiperazine, i.e., α-L-aspartyl-L-phenylalaninediketopiperadine (hereafter simply referred to as "α-AP.DKP") and, large quantities of α-AP.DKP were by-produced during the production steps for producing α-APM in an industrial scale.

Presently, the by-produced α-AP.DKP is completely hydrolyzed together with other by-products such as β-L-aspartyl-L-phenylalanine methyl ester (β-AMP), α- or β-L-aspartyl-L-phenylalanine (α- or β-AP), etc. to recover them as L-aspartic acid and L-phenylalanine. The recovered materials are used as raw materials for synthesis of α-APM. However, when α-APM is intended to produce in an industrial scale, this process results in involved steps for recovery. In addition, the process is very disadvantageous also in view of costs for secondary raw materials and utility consumption.

As a result of extensive investigations with an attempt to improve the foregoing problems, the present inventors have found that α-APM can be directly formed by contacting α-AP.DKP with a strong acid in a solvent mixture comprising methanol and water and, have accomplished the present invention.

The present invention provides a process for producing α-APM in good efficiency.

Hereafter the present invention will be described more in detail.

The contact of α-AP.DKP with the strong acid is generally conducted by suspensing α-AP.DKP in the solvent mixture of methanol and water containing the strong acid and then stirring the suspension or allowing it to stand. By this procedure, the suspension is continuously stir or allowed to stand for a time period sufficieint to cause partial hydrolysis (the partial hydrolysis as used herein refers to a cleavage of one of the peptide bonds in α-AP.DKP), whereby α-APM is directly formed from α-AP.DKP.

The temperature for the contact varies widely from −10° to 150° C. However, when considering the reaction time, ease in operation, etc., the temperature is preferably from 20° to 80° C.

As a matter of course, the time period required for the contact varies depending upon temperature and the concentration of the strong acid. In view of the amount of α-APM to be produced and separation of the unreacted α-AP.DKP from the produced α-APM, the time period necessary for substantially completing the partial hydrolysis of α-AP.DKP is preferred. The unduly prolonged time period for the contact is not preferred since it accelerates the formation of L-aspartic acid and L-phenylalanine due to complete hydrolysis. The time period required for the contact at each temperature and each concentration of the strong acid may be experimentally determined, for example, by measuring the change of the amount of α-APM produced with the passage of time using an amino acid automatic analyzer.

As the water-methanol solvent mixture used in the present invention, the solvent mixture having a molar ratio of methanol to water of 0.01 to 1.0 is used. In case where the molar ratio of methanol to water is lower than 0.01, α-L-aspartyl-L-phenylalanine is produced in large quantities and, in the case where the molar ratio is higher than 1.0, α-L-aspartyl-L-phenylalanine dimethyl ester is produced in large quantities. Such are not preferred.

As the acid to be used, strong acids such as hydrochloric acid, hydrobromic acid, sulfuric acid, etc. can be used. Preferably, hydrohalic acids such as hydrochloric acid, hydrobromic acid, etc. are employed. In the case of using hydrohalic acids, α-APM formed in the reaction solution precipitates directly as α-APM hydrohalide crystals by appropriately choosing the concentration and temperature. Thus, it becomes easy to isolate the crystals (U.S. Pat. No. 3,798,207). Further, in the case of using hydrohalic acids, the thus formed α-APM hydrohalides are formed out of the system as crystals of high purity without being accompanied by other by-products so that the yield is improved. Further, the reaction solvent insufficient to completely dissolve α-AP.DKP is used and, even though the contact is conducted in a suspended state, α-AP.DKP is decomposed with the passage of time to form α-APM hydrohalides. Thus, reaction vessels can be rendered compact. The concentration of the acid used varies depending upon the initial concentration of α-AP.DKP. However, when the strong acid is used in a large excess, complete hydrolysis of α-APM is sometimes accelerated. Accordingly, it is preferred that the concentration of the strong acid be less than 10 M/l.

The formed α-APM or the hydrohalides may be appropriately separated from the reaction liquid in a conventional manner, if necessary. The hydrohalides may also be converted into free α-APM in a conventional manner, if necessary.

As is clear from the foregoing, α-APM can easily be produced directly from α-AP.DKP in a simple manner in accordance with the present invention. Accordingly, the present invention greatly contributes to industry for producing α-APM.

Hereafter the present invention will be described in more detail with reference to the examples below.

In the examples, the analysis of α-APM was carried out using an amino acid autoanalyzer.

EXAMPLE 1

In 200 g of a solvent mixture having a 5.5 M/l concentration of hydrochloric acid and a 0.25 molar ratio of methanol to water (a methanol-water solvent mixture (0.25 in a molar ratio) containing hydrochloric acid in a concentration of 5.5 M/l) was suspended 52.5 g of α-AP.DKP. The suspension was stirred at 80° C. for about 45 minutes, whereby crystals of α-AP.DKP were completely dissolved.

The solution was immediately analyzed and as the result, it was confirmed that 12.3 g of α-APM was formed. The formation yield was 20.9%.

EXAMPLE 2

In 200 g of a solvent mixture having a 7.5 M/l concentration of hydrochloric acid and a 0.1 molar ratio of methanol to water was suspended 52.5 g of α-AP.DKP. The suspension was stirred at 80° C. for about 1 hour, whereby crystals of α-AP.DKP were completely dissolved.

The solution was immediately analyzed and as the result, it was confirmed that 11.3 g of α-APM was formed. The formation yield was 19.2%.

EXAMPLE 3

In 200 g of a solvent mixture having a 5.5 M/l concentration of hydrochloric acid and a 0.1 molar ratio of methanol to water was suspended 52.5 g of α-AP.DKP. The suspension was stirred at 80° C. for about 1.5 hour, whereby crystals of α-AP.DKP were completely dissolved.

A part of the solution was analyzed and as the result, it was confirmed that α-APM was formed.

In order to prevent α-AP.DKP from complete hydrolysis and accelerate the precipitation of α-APM hydrochloride, the solution was immediately cooled. After the solution was stored in a refrigerator for two days and nights, the precipitated crystals were taken out by filtration.

The crystals were identified to be crystals of α-APM hydrochloride because the infrared absorption spectrum of the crystals was identical with that of authetic α-APM hydrochloride. Further the analytical result of the crystals revealed that the α-APM content in the crystals was 23.5 g. The yield for isolation was 39.9%.

EXAMPLE 4

A complete solution of α-AP.DKP crystals was obtained in a manner quite similar to Example 3 except that stirring was conducted at 40° C. for about 4 days in place of the stirring at 80° C. for about 1.5 hour.

The solution was treated in a manner similar to Example 3 to obtain crystals of α-APM hydrochloride.

The α-APM content in the crystals was 25.7 g. The yield for isolation was 43.7%.

EXAMPLE 5

In 200 g of a solvent mixture having a 5.5 M/l concentration of hydrochloric acid and a 0.25 molar ratio of methanol to water was suspended 52.5 g of α-AP.DKP. The suspension was stirred at 80° C. for about 30 minutes, whereby crystals of α-AP.DKP were completely dissolved.

The solution was immediately analyzed and as the result, it was confirmed that 9.0 g of α-APM was formed. The formation yield was 15.3%.

EXAMPLE 6

A complete solution of α-AP.DKP crystals was obtained in a manner quite similar to Example 3 except that hydrobromic acid having a 5.0 M/l concentration was used in place of hydrochloric acid having a 5.5 M/l concentration.

The solution was immediately cooled. After the solution was stored in a refrigerator for two days and nights, the precipitated crystals were taken out by filtration.

The crystals were confirmed to be crystals of α-APM hydrobromide because the infrared absorption spectrum of the crystals was identical with that of authentic α-APM hydrobromide. Further, the α-APM content in the crystals were 21.1 g. The yield for isolation was 35.8%.

What is claimed is:

1. A process for producing α-L-aspartyl-L-phenylalanine methyl ester or its hydrohalide, which comprises contacting 3-benzyl-6-carboxymethyl-2,5-diketopiperazine with a strong acid in a solvent mixture comprising methanol and water for a time period sufficient to cause partial hydrolysis, wherein said contacting is carried out at a temperature of from about 20° C. to about 80° C., wherein the concentration of said strong acid is less than about 10 molar, and wherein the water-methanol solvent has a molar ratio of methanol to water of from about 0.01 to about 1.0.

2. The process of claim 1, wherein the strong acid is hydrochloric acid or hydrobromic acid.

3. The process of claim 1, wherein the strong acid is sulfuric acid.

4. The process of claim 1, wherein said 3-benzyl-6-carboxymethyl-2,5-diketopiperazine is not completely dissolved in said solvent mixture.

* * * * *